(12) United States Patent
Lin et al.

(10) Patent No.: US 7,964,811 B2
(45) Date of Patent: Jun. 21, 2011

(54) MOISTURE-PROOF PUSH-BUTTON SWITCH MODULE

(75) Inventors: Chia-Wei Lin, Taoyuan (TW);
Chi-Meng Phang, Taoyuan (TW);
Chen-Hong Huang, Taoyuan (TW)

(73) Assignee: Solteam Electronics Co., Ltd., Taoyuan (TW)

( * ) Notice: Subject to any disclaimer, the term of this patent is extended or adjusted under 35 U.S.C. 154(b) by 239 days.

(21) Appl. No.: 12/379,885

(22) Filed: Mar. 4, 2009

(65) Prior Publication Data

US 2010/0147659 A1 Jun. 17, 2010

(30) Foreign Application Priority Data

Dec. 17, 2008 (TW) ................................ 97222608 U

(51) Int. Cl.
*H01H 13/06* (2006.01)
(52) U.S. Cl. .................................................. 200/302.2
(58) Field of Classification Search ............... 200/302.2, 200/302.1, 293, 533–535
See application file for complete search history.

(56) References Cited

U.S. PATENT DOCUMENTS

| | | | | |
|---|---|---|---|---|
| 4,324,956 A | * | 4/1982 | Sakakino et al. | 200/16 R |
| 4,628,166 A | * | 12/1986 | Bingo et al. | 200/302.1 |
| 4,877,930 A | * | 10/1989 | Fukuma | 200/302.2 |
| 6,459,057 B1 | * | 10/2002 | Domzalski | 200/302.2 |

* cited by examiner

*Primary Examiner* — Edwin A. Leon
*Assistant Examiner* — Vanessa Girardi
(74) *Attorney, Agent, or Firm* — Roger H. Chu

(57) ABSTRACT

A moisture-proof push-button switch module includes a first casing unit, a second casing unit, a first movable structure, and a push structure. The first casing unit has a first outer moisture-proof structure disposed around its outer side. The first casing unit has a first receiving room, a second receiving room, and an opening communicating between the second receiving room and the external environment. The second casing unit is mated with the first casing unit. The second casing unit has a second outer moisture-proof structure and a first moisture block, and the first outer moisture-proof structure and the second outer moisture-proof structure are mated with each other. The first movable structure has a first movable element mated with the first moisture block. The push structure passes through the opening in order to selectably push the first movable element.

20 Claims, 9 Drawing Sheets

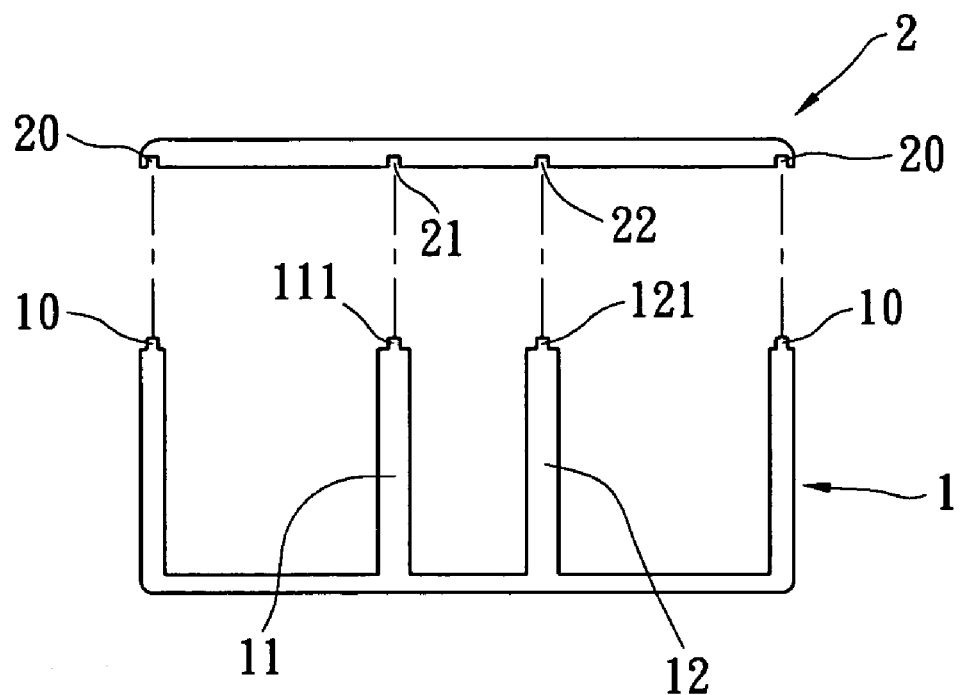
FIG. 1B1
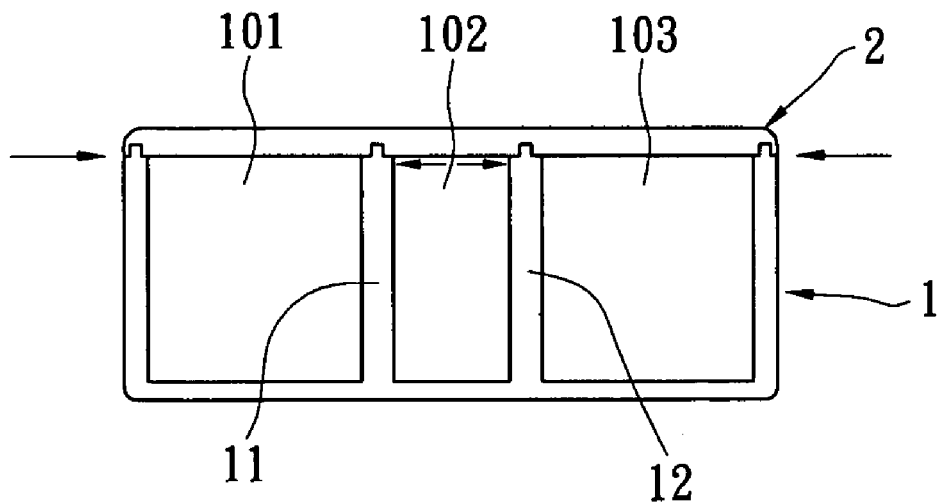
FIG. 1B2

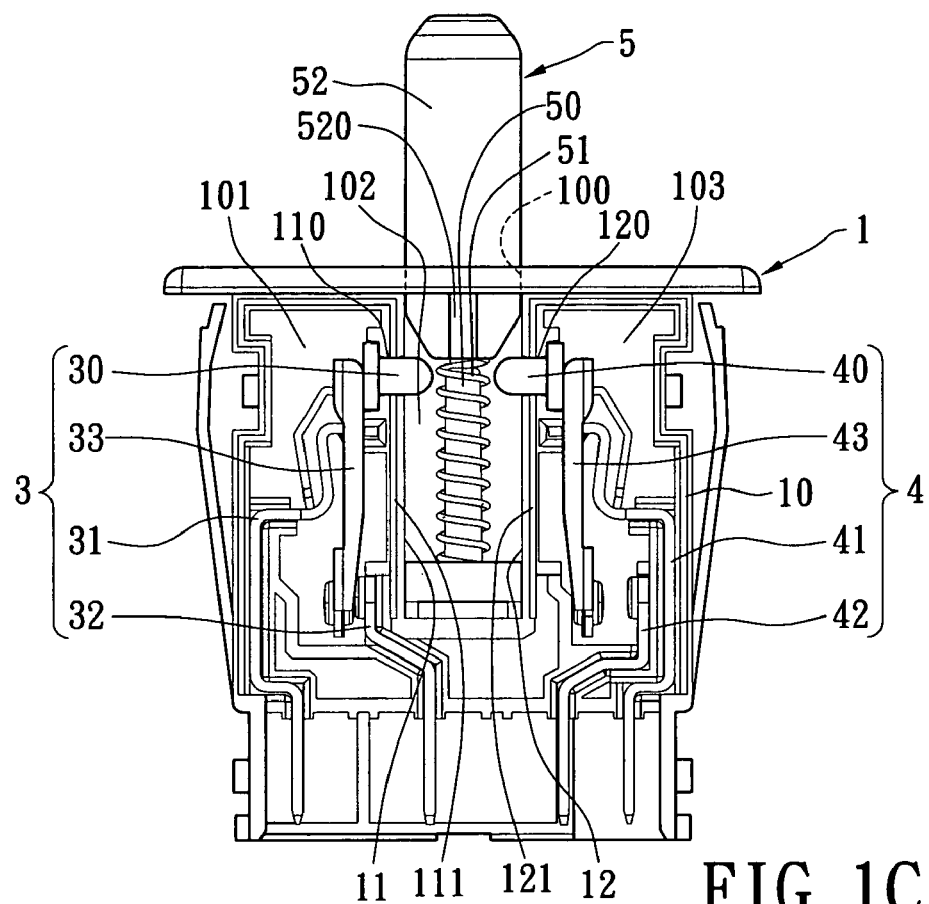
FIG. 1C1
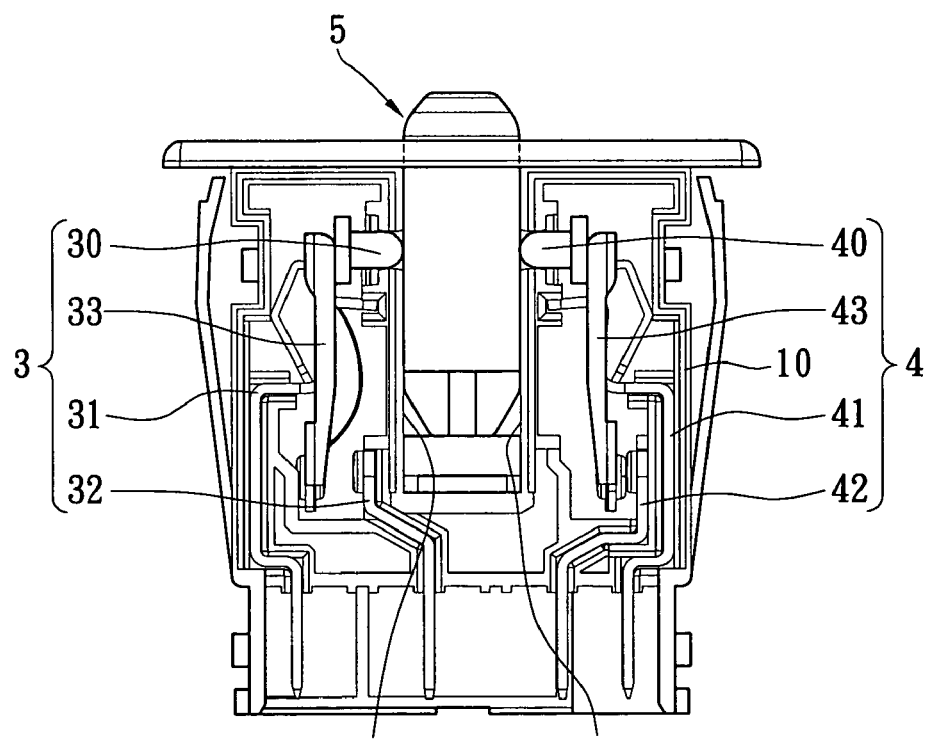
FIG. 1C2

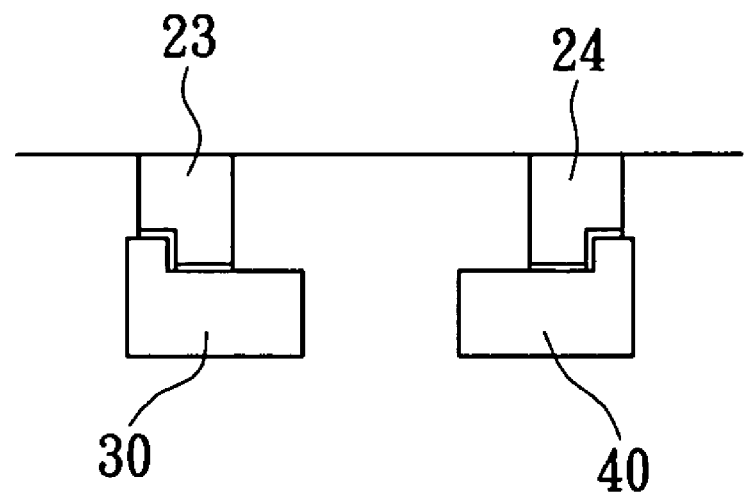
FIG. 1D1
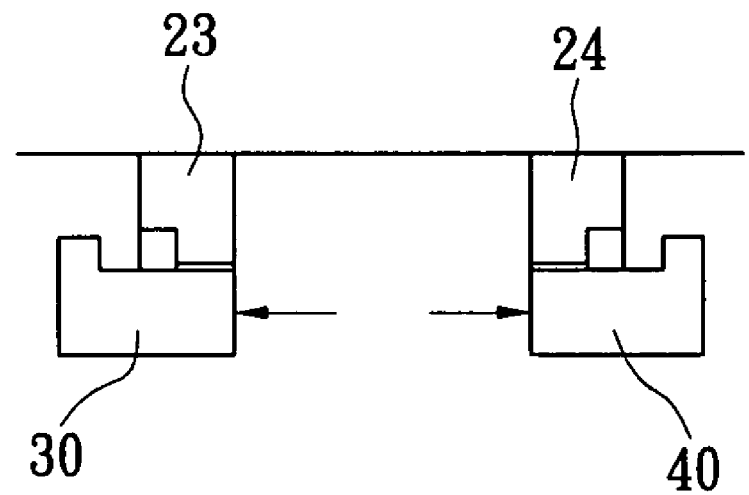
FIG. 1D2

MOISTURE-PROOF PUSH-BUTTON SWITCH MODULE

BACKGROUND OF THE INVENTION

1. Field of the Invention

The present invention relates to a push-type switch module, and particularly relates to a moisture-proof push-button switch module.

2. Description of Related Art

Electronic devices are popularly applied to daily living due to commercial and industrial progress. Hence, switch is an important component of electronic device to control the functions of the electronic device. In the general environment, the switch does not need to use the design of waterproof function. However, for high-level electronic device, the switch needs to use the design of waterproof function with different grades.

However, most of push-type switches do not have any waterproof function in business situations. Hence, most push-type switches may get rusty easily due to the environment. For example, when water or moisture enters the push-type switch, the circuit of the push-type switch may rust and cause a short circuit. This reduces the service life and the work efficiency of the push-type switch.

In order to achieve water resistance, the push-type switch of the prior art uses a flexible water proof sheath disposed around its outer surface. However, the flexible waterproof sheath may become rubbed off and brake easily after a long time of use of the push-type switch, and the circuit of the push-type switch would become rusty under the effect of water or moisture and cause a short circuit. In addition, the flexible waterproof sheath of the prior art does not have a telescopic portion to protect the curved portion and the corner portion of the push-type switch. Thus, the flexible waterproof sheath may easily become rubbed off or broken after long time usage.

SUMMARY OF THE INVENTION

One particular aspect of the present invention is to provide a moisture-proof push-button switch module. The present invention has many moisture-proof structures that can prevent some metal elements from rusting under the effect of external moisture. Hence, the prevent invention can maintain its switch function by using the combination selected from the moisture-proof structures moisture-proof structures. Moreover, the present invention can control more than two movable structures (two switch structures) at the same time.

In order to achieve the above-mentioned aspects, the present invention provides a moisture-proof push-button switch module, including: a first casing unit, a second casing unit, at least one first movable structure, and a push structure. The first casing unit has a first outer moisture-proof structure disposed around its outer side. The first casing unit has a first receiving room, a second receiving room, a first blocking wall disposed between the first receiving room and the second receiving room, a first communicating opening passing through the first blocking wall and communicating between the first receiving room and the second receiving room, and an opening communicating between the second receiving room and the external environment. The second casing unit is mated with the first casing unit. The second casing unit has a second outer moisture-proof structure and a first moisture block, and the first outer moisture-proof structure and the second outer moisture-proof structure are mated with each other. The first movable structure is disposed in the first receiving room. The first movable structure has a first movable element movably disposed in the first communicating opening, and the first movable element is mated with the first moisture block. The push structure passes through the opening in order to selectably push the first movable element.

Therefore, the moisture-proof structures of the present invention can prevent some metal elements such as the first movable element and the second movable element from rusting under the effect of external moisture. Moreover, the present invention can design many movable structures (many switch structures), and the movable structures can be controlled at the same time by pressing the push structure.

It is to be understood that both the foregoing general description and the following detailed description are exemplary, and are intended to provide further explanation of the invention as claimed. Other advantages and features of the invention will be apparent from the following description, drawings and claims.

BRIEF DESCRIPTION OF THE DRAWINGS

The various objectives and advantages of the present invention will be more readily understood from the following detailed description when read in conjunction with the appended drawings, in which:

FIG. 1B1 is a lateral, exploded, schematic view of a first casing unit mated with a second casing unit according to the first embodiment of the present invention;

FIG. 1B2 is a lateral, assembled, schematic view of a first casing unit mated with a second casing unit according to the first embodiment of the present invention;

FIG. 1C1 is a partial, top, assembled, schematic view of a moisture-proof push-button switch module according to the first embodiment of the present invention (before pressing the push structure);

FIG. 1C2 is a partial, top, assembled, schematic view of a moisture-proof push-button switch module according to the first embodiment of the present invention (after pressing the push structure);

FIG. 1D1 is a lateral, schematic view of a first movable element and a second movable element both that have not been moved according to the first embodiment of the present invention (before pressing the push structure);

FIG. 1D2 is a lateral, schematic view of a first movable element and a second movable element both that have been moved according to the first embodiment of the present invention (after pressing the push structure);

FIG. 2 is a lateral, exploded, schematic view of a first casing unit mated with a second casing unit according to the second embodiment of the present invention;

DETAILED DESCRIPTION OF THE PREFERRED EMBODIMENTS

Figure 1A:
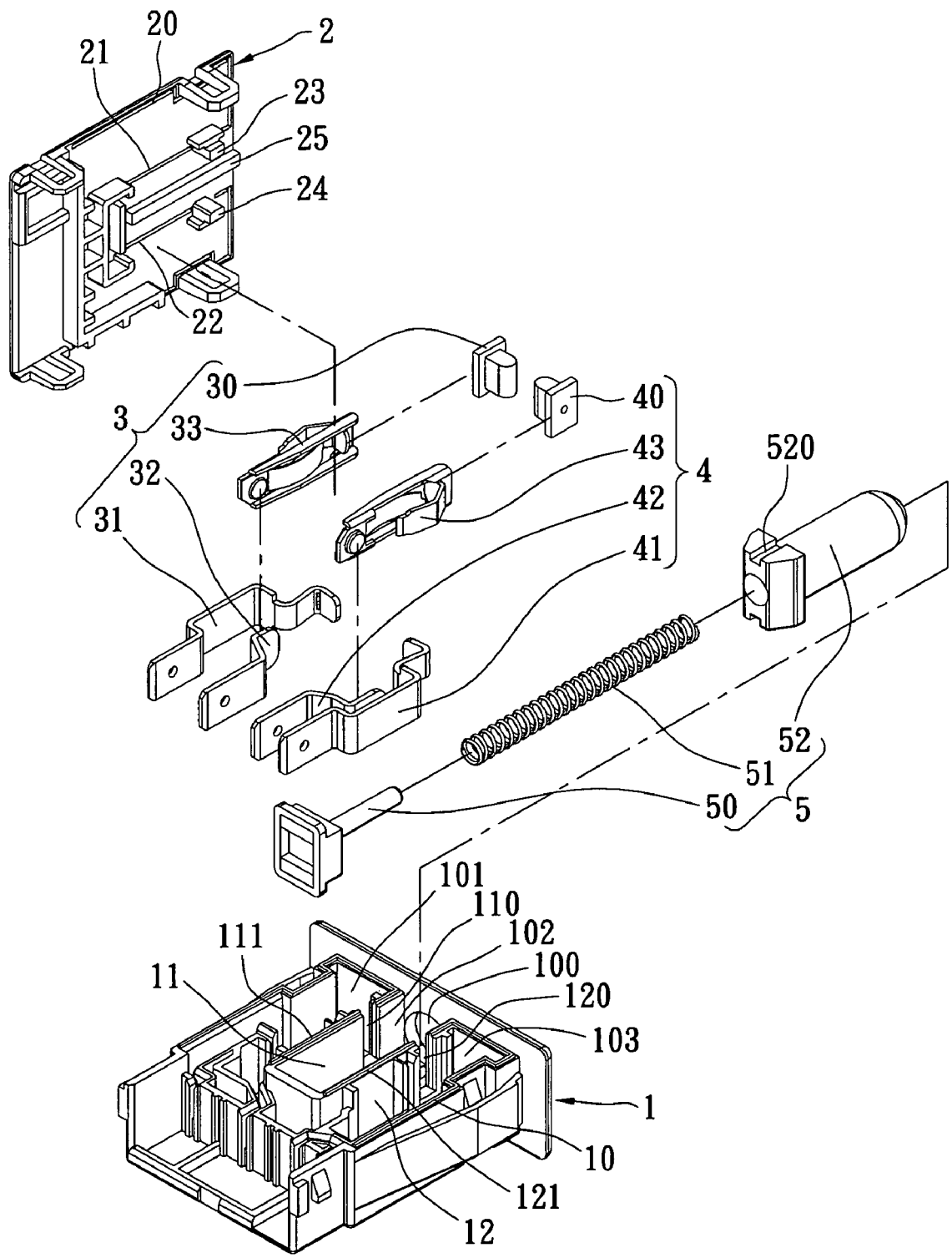
FIG. 1A is a perspective, exploded, schematic view of a moisture-proof push-button switch module according to the first embodiment of the present invention.

Referring to FIGS. 1A to 1E, the first embodiment of the present invention provides a moisture-proof push-button switch module, including: a first casing unit 1, a second casing unit 2, at least one first movable structure 3, at least one second movable structure 4 and a push structure 5.

The first casing unit 1 has a first outer moisture-proof structure 10 disposed around its outer side. The first casing unit 1 has a first receiving room 101, a second receiving room 102, a third receiving room 103, a first blocking wall 11, a first communicating opening 110, a second blocking wall 12, a second communicating opening 120 and an opening 100. The first blocking wall 11 is disposed between the first receiving room 101 and the second receiving room 102, and the first communicating opening 110 passes through the first blocking wall 11 and communicating between the first receiving room 101 and the second receiving room 102. The second blocking wall 12 is disposed between the second receiving room 102 and the third receiving room 103, and a second communicating opening 120 passes through the second blocking wall 12 and communicating between the second receiving room 102 and the third receiving room 103. The opening 100 communicates between the second receiving room 120 and the external environment.

Figure 1B:
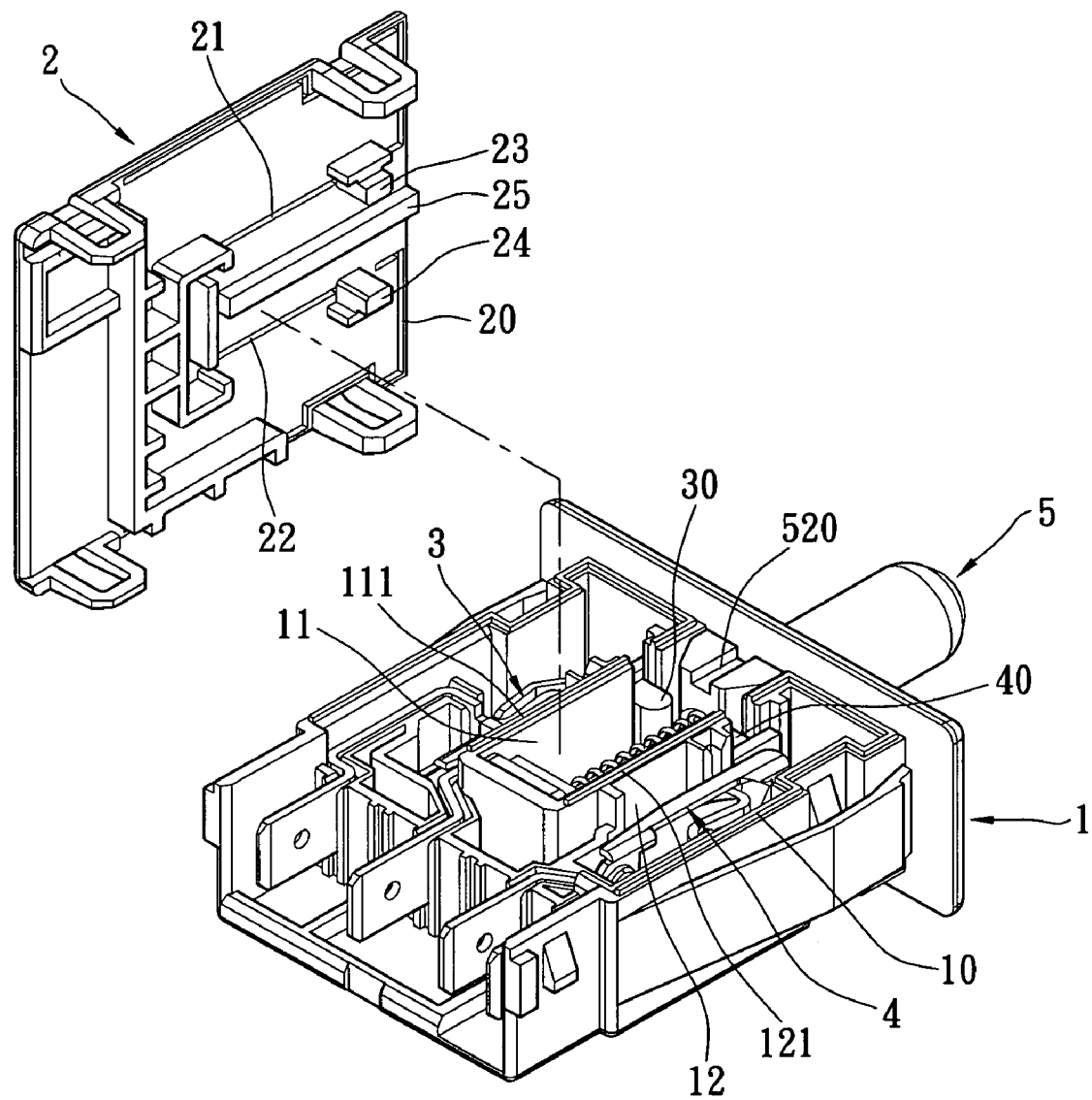
FIG. 1B is a partial, assembled, schematic view of a moisture-proof push-button switch module according to the first embodiment of the present invention.
Figure 1E:
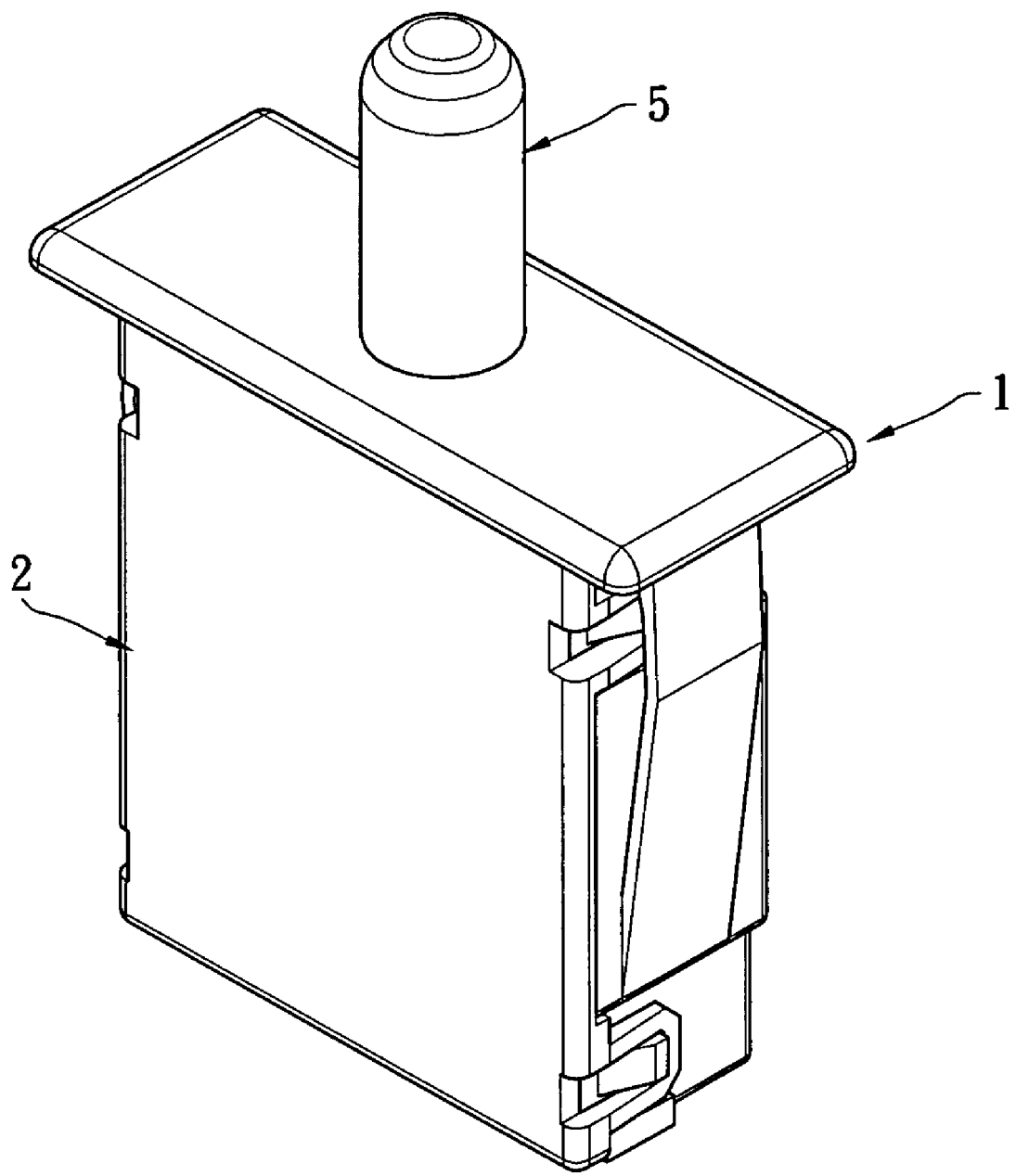
FIG. 1E is a perspective, assembled, schematic view of a moisture-proof push-push-button switch module according to the first embodiment of the present invention.

Moreover, the second casing unit 2 is mated with the first casing unit 1. The second casing unit 2 has a second outer moisture-proof structure 20, two second inner moisture-proof structures (21, 22), a first moisture block 23 and a second moisture block. In addition, the first outer moisture-proof structure 10 and the second outer moisture-proof structure 20 are mated with each other in order to prevent outer moisture from entering the first receiving room 101 and the third receiving room 103. In the first embodiment, the first outer moisture-proof structure 10 is at least one convex structure, and the second outer moisture-proof structure 20 is at least one concave structure (as shown in FIG. 1B1). Hence, the first outer moisture-proof structure 10 (convex structure) and the second outer moisture-proof structure 20 (concave structure) are mated with each other in order to prevent outer moisture (shown as the straight external arrows in FIG. 1B2) from passing through a joint between the first casing unit 1 and the second casing unit 2 to enter the first receiving room 101 and the third receiving room 103. However, the shapes of the first outer moisture-proof structure 10 and the second outer moisture-proof structure 20 are just examples and do not limit the present invention.

Furthermore, the first blocking wall 11 has a first inner moisture-proof structure 111, and the first inner moisture-proof structure 111 (such as a convex structure) is mated with the second inner moisture-proof structure 21 (such as a concave structure) of the second casing unit 2 each other (as shown in FIG. 1B1) in order to present the external moisture that has entered the second receiving room 102 (shown as the inner arrows in FIG. 1B2) from passing through a joint between the first blocking wall 11 and the second casing unit 2 to enter the first receiving room 101.

In addition, the second blocking wall 12 has a first inner moisture-proof structure 121, and the first inner moisture-proof structure 121 is mated with the second inner moisture-proof structure 22 of the second casing unit 2 each other (as shown in FIG. 1B1) in order to prevent the external moisture that has entered the second receiving room 102 (shown as the inner arrows in FIG. 1B2) from passing through a joint between the second blocking wall 12 and the second casing unit 2 to enter the third receiving room 103.

Moreover, the first movable structure 3 is disposed in the first receiving room 101. The first movable structure 3 has a first movable element 30 movably disposed in the first communicating opening 110. The first movable element 30 is mated with the first moisture block 23 each other (as shown in FIGS. 1C1 and 1D1) in order to prevent the external moisture that has entered the second receiving room 102 from going to the first receiving room 101. In other words, the first movable element 30 and the first moisture block 23 are mated with each other in order to prevent the external moisture that has entered the second receiving room 102 from passing through a joint between the first movable element 30 and the first moisture block 23 to enter the first receiving room 101.

Figure 2:
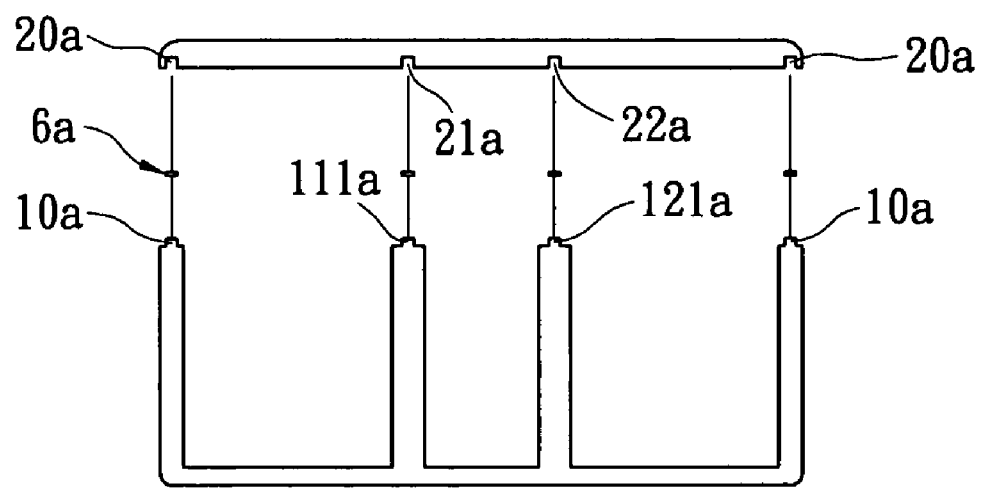

Furthermore, the first movable structure 3 has a first conductive element 31, a second conductive element 32, and a conductive movable element 33 selectably electrically connected between the first conductive element 31 and the second conductive element 32 by driving the first movable element 30, so that the first conductive element 31 and the second conductive element 32 are selectably contacted with or separated from each other by the conductive movable element 33 (as shown in FIGS. 1C1 and 1C2). In the first embodiment, one side of the conductive movable element 33 is electrically connected with the first conductive element 31, and another side of the conductive movable element 33 is selectably electrically connected with the second conductive element 32 by driving the first movable element 30. Hence, when another side of the conductive movable element 33 is electrically connected to the second conductive element 32, the first conductive element 31 and the second conductive element 32 are electrically connected with each other; when another side of the conductive movable element 33 does not be electrically connected to the second conductive element 32, the first conductive element 31 and the second conductive element 32 are insulated from each other.

However, the feature of the first conductive element 31 and the second conductive element 32 selectably contacted with or separated from each other (ON/OFF) by the conductive movable element 33 is just an example. For example, two conductive elements can be selectably separated from or contacted with each other (OFF/ON) by controlling the conductive movable element 33; alternatively, one conductive element is selectably electrically two conductive elements (ON/ON) by controlling the conductive movable element 33.

Moreover, the second movable structure 4 is disposed in the third receiving room 103. The second movable structure 4 has a second movable element 40 movably disposed in the second communicating opening 120. The second movable element 40 is mated with the second moisture block 24 each other (as shown in FIGS. 1C1 and 1D1) in order to prevent the external moisture that has entered the second receiving room 102 from going to the third receiving room 103. In other words, the second movable element 40 and the second moisture block 24 are mated with each other in order to prevent the external moisture that has entered the second receiving room 102 from passing through a joint between the second movable element 40 and the second moisture block 24 to enter the third receiving room 103.

Furthermore, the second movable structure 4 has a first conductive element 41, a second conductive element 42, and a conductive movable element 43 selectably electrically connected between the first conductive element 41 and the second conductive element 42 by driving the second movable element 40, so that the first conductive element 41 and the second conductive element 42 are selectably contacted with or separated from each other by the conductive movable element 43 (as shown in FIGS. 1C1 and 1C2). In the first embodiment, one side of the conductive movable element 43 is electrically connected with the first conductive element 41, and another side of the conductive movable element 43 is selectably electrically connected with the second conductive element 42 by driving the second movable element 40. Hence, when another side of the conductive movable element 43 is electrically connected to the second conductive element 42, the first conductive element 41 and the second conductive element 42 are electrically connected with each other; when another side of the conductive movable element 43 does not be electrically connected to the second conductive element 42, the first conductive element 41 and the second conductive element 42 are insulated from each other.

However, the feature of the first conductive element 41 and the second conductive element 42 selectably contacted with or separated from each other (ON/OFF) by the conductive movable element 43 is just an example. For example, two conductive elements can be selectably separated from or contacted with each other (OFF/ON) by controlling the conductive movable element 43; alternatively, one conductive element is selectably electrically two conductive elements (ON/ON) by controlling the conductive movable element 43.

Moreover, the first movable element 30 can be an L-shaped movable body, and the first moisture block 23 can be an L-shaped fixed body (such as FIG. 1D1). Hence, when the first movable element 30 is pushed by an external force (shown as the arrow in FIG. 1D2), the first movable element 30 (the L-shaped movable body) and the first moisture block 23 (the L-shaped fixed body) are slidably mated to each other. Therefore, the present invention can prevent the external moisture that has entered the second receiving room 102 from passing through a joint between the first movable element 30 and the first moisture block 23 to enter the first receiving room 101.

Furthermore, the second movable element 40 can be an L-shaped movable body, and the second moisture block 24 can be an L-shaped fixed body (such as FIG. 1D1). Hence, when the second movable element 40 is pushed by an external force (shown as the arrow in FIG. 1D2), the second movable element 40 (the L-shaped movable body) and the second moisture block 24 (the L-shaped fixed body) are slidably mated to each other. Therefore, the present invention can prevent the external moisture that has entered the second receiving room 102 from passing through a joint between the second movable element 40 and the second moisture block 24 to enter the third receiving room 103.

In addition, the push structure 5 has a shaft portion 50 positioned in the second receiving room 102, a flexible element 51 disposed around the shaft portion 50, and a push body 52 disposed above the flexible element 51 in order to press the flexible element 51. One part (bottom part) of the push body 52 is limited in the first casing unit 1, so that the push body 52 cannot be separated from the opening 100. Moreover, the push structure 5 can pass through the opening 100 in order to selectably push the first movable element 3 and the second movable element 4 (such as FIG. 1C2). In other words, the push body 52 of the push structure 5 passes through the opening 100 and when the push body 52 is pushed downwards by an external force, the edge of the push body 52 can push the first movable element 30 and the second movable element 40 to move at the same time. When the external force is removed from the push body 52, the push body 52 can be restored to the original position by the elasticity of the flexible element 51.

Furthermore, the push body 52 has a first guiding portion 520, and the second casing unit 2 has a second guiding portion 25 mated with the first guiding portion 520 each other. Hence, the push body 52 is smoothly guided and moved in the second receiving room 102 by the second guiding portion 25 by matching the first guiding portion 520 and the first guiding portion 25.

In addition, the first casing unit 1 further includes another blocking wall disposed between the first blocking wall 11 and the second blocking wall 12. The three blocking walls are combined to form a U-shaped convex block. Moreover, the present invention includes a bottom seat disposed under the shaft portion 50 and abutted against another above-mentioned blocking wall. The second casing unit 2 has a protrusion mated with above-mentioned blocking wall and the bottom seat. Hence, the present invention can prevent the moisture from passing through a joint between above-mentioned blocking wall and the second casing unit 2 by matching the protrusion, above-mentioned blocking wall and the bottom seat.

The moisture-proof structures of the present invention can prevent some metal elements such as the first movable element 3 (the first conductive element 31, the second conductive element 32 and the conductive movable element 33) and the second movable element 4 (the first conductive element 41, the second conductive element 42 and the conductive movable element 43) from rusting under the effect of external moisture. Hence, the prevent invention can maintain its switch function by using any combination selected from the moisture-proof structures moisture-proof structures.

Referring to FIG. 2, the difference between the second embodiment and the first embodiment is that: in the second embodiment, the push-button switch module further comprises a flexible structure 6a disposed between the first outer moisture-proof structure 10a (the convex structure) and the second outer moisture-proof structure 20a (the concave structure). In addition, the flexible structure 6a also can be disposed between the first inner moisture-proof structure 111a and the second inner moisture-proof structure 21a and between the first inner moisture-proof structure 121a and the second inner moisture-proof structure 22a.

Figure 3:
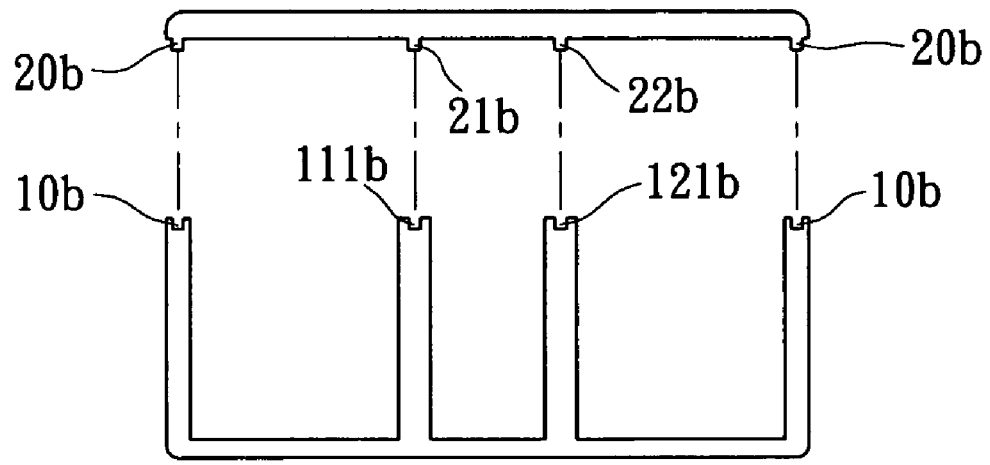
FIG. 3 is a lateral, exploded, schematic view of a first casing unit mated with a second casing unit according to the third embodiment of the present invention.

Referring to FIG. 3, the difference between the third embodiment and the first embodiment is that: in the third embodiment, the first outer moisture-proof structure 10b can be at least one concave structure, and the second outer moisture-proof structure 20b can be at least one convex structure. In addition, the two first inner moisture-proof structures (111b, 121b) both are concave structures, and the second inner moisture-proof structures (21b, 22b) both are convex structures.

Figure 4:
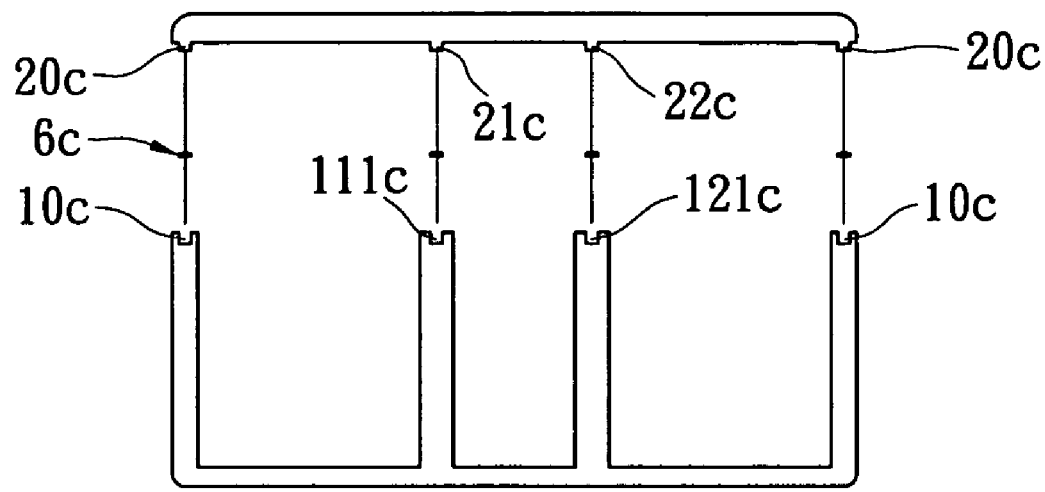
FIG. 4 is a lateral, exploded, schematic view of a first casing unit mated with a second casing unit according to the fourth embodiment of the present invention.

Referring to FIG. 4, the difference between the fourth embodiment and the third embodiment is that: in the fourth embodiment, the push-button switch module further comprises a flexible structure 6c disposed between the first outer moisture-proof structure 10c (the concave structure) and the second outer moisture-proof structure 20c (the convex structure). In addition, the flexible structure 6c also can be disposed between the first inner moisture-proof structure 111c and the second inner moisture-proof structure 21c and between the first inner moisture-proof structure 121c and the second inner moisture-proof structure 22c.

Figure 5:
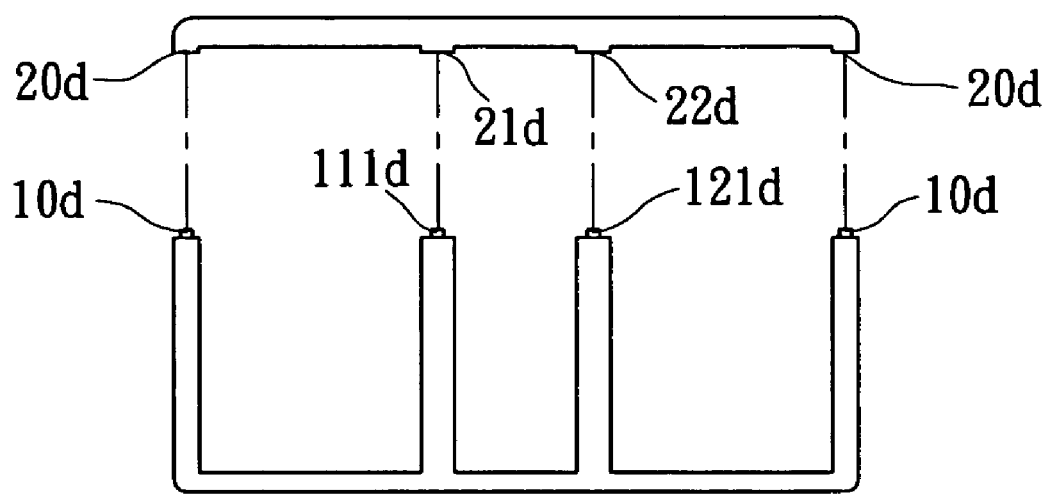
FIG. 5 is a lateral, exploded, schematic view of a first casing unit mated with a second casing unit according to the fifth embodiment of the present invention.

Referring to FIG. 5, the difference between the fifth embodiment and other embodiments is that: in the fifth embodiment, the first outer moisture-proof structure 10d can be a flexible structure, and the second outer moisture-proof structure 20d can be a plane structure. In addition, the two first inner moisture-proof structures (111d, 121d) both are flexible structures, and the second inner moisture-proof structures (21d, 22d) both are plane structures.

Figure 6:
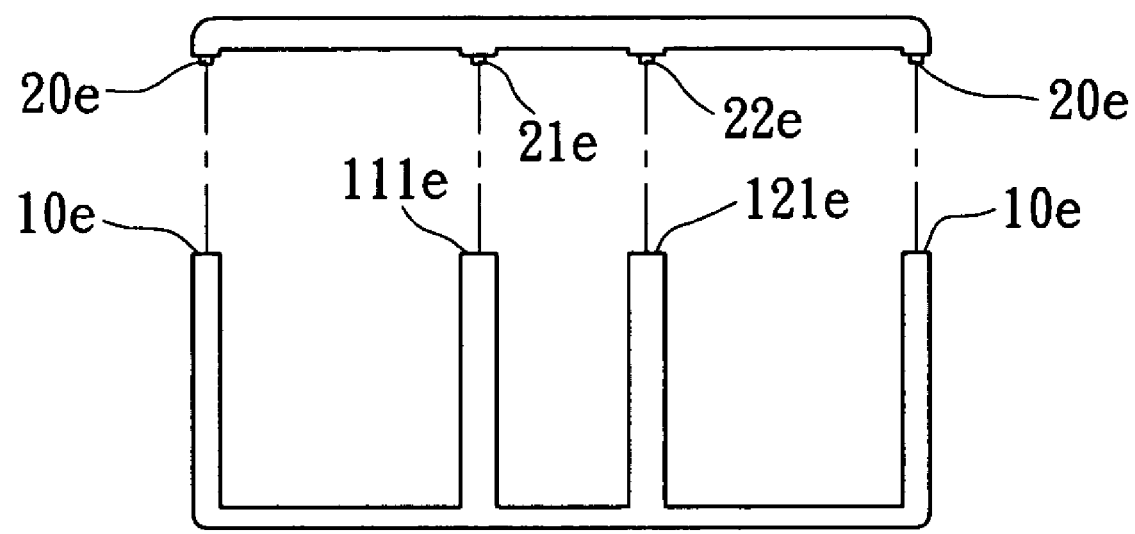
FIG. 6 is a lateral, exploded, schematic view of a first casing unit mated with a second casing unit according to the sixth embodiment of the present invention.

Referring to FIG. 6, the difference between the sixth embodiment and the fifth embodiments is that: in the sixth embodiment, the first outer moisture-proof structure 10e can be a plane structure, and the second outer moisture-proof structure 20e can be a flexible structure. In addition, the two first inner moisture-proof structures (111e, 121e) both are plane structures, and the second inner moisture-proof structures (21e, 22e) both are flexible structures.

Although the present invention has been described with reference to the preferred best molds thereof, it will be understood that the present invention is not limited to the details thereof. Various substitutions and modifications have been suggested in the foregoing description, and others will occur to those of ordinary skill in the art. Therefore, all such substitutions and modifications are intended to be embraced within the scope of the present invention as defined in the appended claims.

What is claimed is:

1. A moisture-proof push-button switch module, comprising:
    a first casing unit having a first outer moisture-proof structure disposed around its outer side, wherein the first casing unit has a first receiving room, a second receiving room, a first blocking wall disposed between the first receiving room and the second receiving room, a first communicating opening passing through the first blocking wall and communicating between the first receiving room and the second receiving room, and an opening communicating between the second receiving room and the external environment;
    a second casing unit mated with the first casing unit, wherein the second casing unit has a second outer moisture-proof structure and a first moisture block, and the first outer moisture-proof structure and the second outer moisture-proof structure are mated with each other;
    at least one first movable structure disposed in the first receiving room, wherein the first movable structure has a first movable element movably disposed in the first communicating opening, and the first movable element is mated with the first moisture block; and
    a push structure passing through the opening in order to selectably push the first movable element.

2. The push-button switch module as claimed in claim 1, wherein the first outer moisture-proof structure is at least one convex structure, and the second outer moisture-proof structure is at least one concave structure.

3. The push-button switch module as claimed in claim 2, further comprising: a flexible structure disposed between the convex structure and the concave structure.

4. The push-button switch module as claimed in claim 1, wherein the first outer moisture-proof structure is at least one concave structure, and the second outer moisture-proof structure is at least one convex structure.

5. The push-button switch module as claimed in claim 4, further comprising: a flexible structure disposed between the concave structure and the convex structure.

6. The push-button switch module as claimed in claim 1, wherein the first outer moisture-proof structure is a flexible structure, and the second outer moisture-proof structure is a plane structure.

7. The push-button switch module as claimed in claim 1, wherein the first outer moisture-proof structure is a plane structure, and the second outer moisture-proof structure is a flexible structure.

8. The push-button switch module as claimed in claim 1, wherein the first blocking wall has a first inner moisture-proof structure, and the second casing unit has a second inner moisture-proof structure mated with the first inner moisture-proof structure each other.

9. The push-button switch module as claimed in claim 8, wherein the first inner moisture-proof structure is at least one convex structure, and the second inner moisture-proof structure is at least one concave structure.

10. The push-button switch module as claimed in claim 9, further comprising: a flexible structure disposed between the convex structure and the concave structure.

11. The push-button switch module as claimed in claim 8, wherein the first inner moisture-proof structure is at least one concave structure, and the second inner moisture-proof structure is at least one convex structure.

12. The push-button switch module as claimed in claim 11, further comprising: a flexible structure disposed between the concave structure and the convex structure.

13. The push-button switch module as claimed in claim 8, wherein the first inner moisture-proof structure is a flexible structure, and the second inner moisture-proof structure is a plane structure.

14. The push-button switch module as claimed in claim 8, wherein the first inner moisture-proof structure is a plane structure, and the second inner moisture-proof structure is a flexible structure.

15. The push-button switch module as claimed in claim 1, wherein the first movable element is an L-shaped movable body, and the first moisture block is an L-shaped fixed body.

16. The push-button switch module as claimed in claim 1, wherein the first movable structure has a first conductive element, a second conductive element and a conductive movable element selectably electrically connected between the first conductive element and the second conductive element by driving the first movable element, so that the first conductive element and the second conductive element are selectably contacted with or separated from each other by the conductive movable element.

17. The push-button switch module as claimed in claim 1, wherein the push structure has a shaft portion positioned in the second receiving room, a flexible element disposed around the shaft portion and a push body disposed above the flexible element in order to press the flexible element.

18. The push-button switch module as claimed in claim 17, wherein the push body has a first guiding portion, and the second casing unit has a second guiding portion mated with the first guiding portion each other.

19. The push-button switch module as claimed in claim 1, wherein the first casing unit has a third receiving room, a second blocking wall disposed between the second receiving room and the third receiving room, and a second communicating opening passing through the second blocking wall and communicating between the second receiving room and the third receiving room, and the second casing unit has a second moisture block.

20. The push-button switch module as claimed in claim 19, further comprising: at least one second movable structure disposed in the third receiving room, wherein the second movable structure has a second movable element movably disposed in the second communicating opening, and the second movable element is mated with the second moisture block; the push structure passes through the opening in order to selectably push the second movable element; the second blocking wall has a first inner moisture-proof structure, and the second casing unit has a second inner moisture-proof structure mated with the first inner moisture-proof structure each other.

* * * * *